United States Patent
Wang et al.

(10) Patent No.: US 6,733,436 B2
(45) Date of Patent: May 11, 2004

(54) DETACHABLE COMBINATION INSTRUMENT FOR HEALTH-CARE AND TREATMENT

(76) Inventors: Jian Wang, B-2, Building A, Century Garden Nam men wai Ave., Nan kai District, Tian Jin City (CN), 300100; Jingyi Wang, B-2, Building A, Century Garden Nan men wai Ave., Nan kai District, Tian Jin City (CN), 300100

(*) Notice: Subject to any disclaimer, the term of this patent is extended or adjusted under 35 U.S.C. 154(b) by 0 days.

(21) Appl. No.: 10/292,892

(22) Filed: Nov. 12, 2002

(65) Prior Publication Data

US 2004/0010179 A1 Jan. 15, 2004

(30) Foreign Application Priority Data

Jul. 9, 2002 (CN) .................................. 02239676 U

(51) Int. Cl.[7] .............................. A61N 1/00; A61H 1/00
(52) U.S. Cl. .............................. 600/9; 600/15; 607/100; 601/15
(58) Field of Search ................ 600/9–15; 607/108–112, 607/96, 98, 100; 601/15, 66, 67, 69, 70, 113

(56) References Cited

U.S. PATENT DOCUMENTS

| | | | | |
|---|---|---|---|---|
| 5,478,303 A | * | 12/1995 | Foley-Nolan et al. | 600/15 |
| 5,882,292 A | * | 3/1999 | Miyaguchi | 600/9 |
| 6,155,966 A | * | 12/2000 | Parker | 600/13 |
| 6,383,129 B1 | * | 5/2002 | Ardizzone et al. | 600/9 |
| 6,461,377 B1 | * | 10/2002 | An | 607/96 |

* cited by examiner

Primary Examiner—John P. Lacyk
(74) Attorney, Agent, or Firm—Holland & Knight LLP

(57) ABSTRACT

Disclosed is a detachable combination health-care and treatment instrument has a optimal matching parameter, fits the shape of different parts of body, can be used in several parts of body simultaneously, and possesses a energy field multiplexed by a permanent magnetic field, a pulse magnetic field, a thermal effect and far infrared rays. It relates to a health-care and treatment instrument. The instrument includes a main unit, panel units and soft units. In the case of the panel unit, the magnetic induction intensity is 100~130 mT, the inductance of the coil and the core is 30~80 mH, and the impedance of the heater panel is 3~5Ω. In the case of the soft unit, the magnetic induction intensity is ≧100 mT, the inductance of the coil and the core is 30~80 mH, and the impedance of the sheet heater is 7~9Ω. Since the present invention has a plurality of panel units and soft units, several parts of body can be positioned into a multiplex energy field simultaneously so that the communication effect of the venation gets better. Furthermore, since it has the optimal matching parameter and adapts the said multiplex energy field to the body so as to achieve the perfect effect of jingluo conduction and health care.

11 Claims, 5 Drawing Sheets

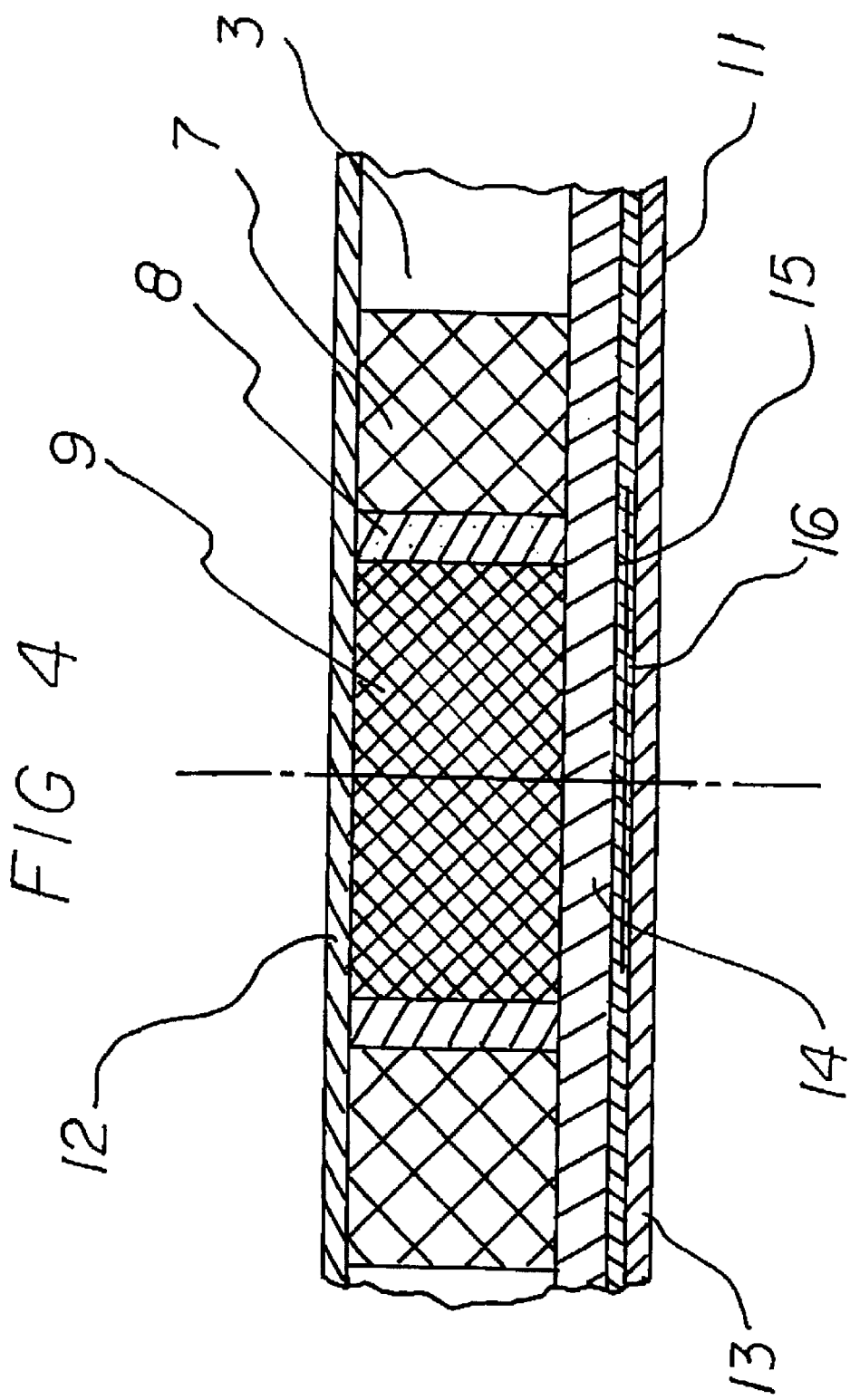

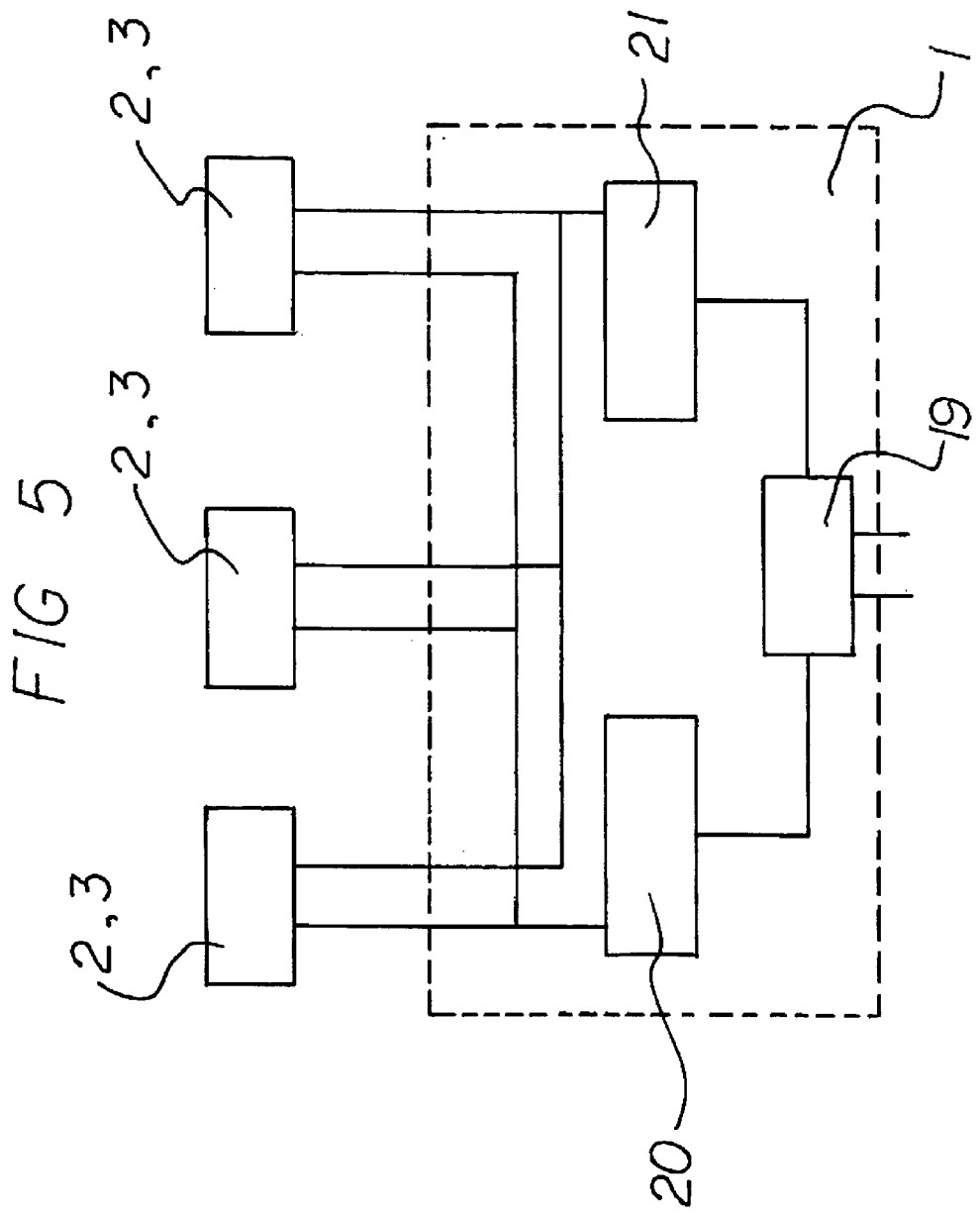

DETACHABLE COMBINATION INSTRUMENT FOR HEALTH-CARE AND TREATMENT

RELATED APPLICATION DATA

This application claims priority from Chinese Patent Application Filing Number 02 2 39676.4 entitled "Detachable Combination Instrument for Health-care and Treatment" filed on Jul. 9, 2002, the contents of which are incorporated herein by reference.

BACKGROUND OF THE INVENTION

1. Field of the Invention

The present invention relates to a health-care and treatment instrument, and in particular to a detachable combination health-care and treatment instrument which is adapted for parts of the body with different forms and that can be used on several portions of the body simultaneously and that has a multiplex energy field consisting of a permanent magnetic field, a pulse magnetic field, and thermal effect and far infrared rays.

2. Description of the Related Art

At present, such an instrument of health care and treatment utilizing a multiplex energy field formed by a permanent magnetic field, a pulse magnetic field and a field of a thermal effect and far infrared rays has been widely used and achieved favorable effect. As an instrument for health care and treatment, it is capable of relieving various pains and building up one's health. However, when applied to a human body, such a health-care and treatment instrument mounted within a fixed shell is not easily and conveniently used on portions of the human body that may be bent. When applied to more than one part of the human body, the instrument must be separately and consecutively applied to each body part, excessively increasing application time. Furthermore, since the instrument may not be applied to separate parts of the human body simultaneously, they are unable to be within the field of complex energy, and it does not effect better results of the jingluo (venation of main and collateral channels via which energy circulates around human body according to Chinese medical theory) conduction. More importantly, the instruments of the like as currently used do not have the optimal combination of intensities of various energy fields, and therefore can not achieve the best results.

SUMMARY OF THE INVENTION

The object of the present invention is to provide a detachable combination health-care and treatment instrument having an optimal combination of energy fields and an appropriate configuration suitable for the shapes of different parts of the human body. The present invention can be applied simultaneously onto plural parts of the human body and possesses an energy field multiplexed by a permanent magnetic field, a pulse magnetic field, and thermal effect and far-infrared rays.

The present invention includes a main unit, a plurality of panel units and a soft unit, where the main unit is connected to the panel units and the soft unit by plugs and jacks, as shown in FIG. 1.

A plurality of panel units or soft units can be connected with the main unit by plugs and jacks respectively. In addition, the main unit can be connected with either panel units or soft units independently.

The main unit includes a shell, a switch and power system, a temperature control system, a pulse magnetic control system, and key-display control system, in which, the switch and power system can be adapted to alternating current (AC) or direct current (DC). When the switch and power system include a plug and a power adapter, the instrument can be used in a household and a vehicle.

Referring to FIG. 2, the panel unit includes a shell, circular magnets, coils, iron cores and a heater panel, wherein a far-infrared ceramic powder adhesive layer is coated on the upper side of the upper layer of the shell and an insulating panel is set beneath the upper layer of the shell. The circular magnets are fixed in the shell, and have magnetic induction of 100–130 mT. Each panel unit may have one or more circular magnets and the magnetic poles of two adjacent circular magnets are opposite. A coil is positioned at the center of the circular magnet, the center of the coil is provided with an iron core, having the inductance of 30–80 mH. An insulating panel is provided between the heater panel and the shell, and the impedance of the heater is 3–5$\Omega$. The heater panel may be formed by arranging a heating wire twisted into a flat disc on one side of the insulating panel. The coil and the heater panel are connected with the jack of main unit through the wire lead and the plug.

Referring to FIG. 3 and FIG. 4, the soft unit includes an upper side layer and a lower side layer, a support member, circular magnets, coils, iron cores and a sheet heater, wherein the outside of the lower side layer is covered by a far infrared ceramic powder adhesive layer, which can be a fibre fabric containing far infrared ceramic powder, or a leather or a fabric (such as wood, hemp, chemical fiber etc.) coated with a far infrared ceramic powder adhesive layer. The support member provided between the upper side layer and the lower side layer can be made of tough material such as plastic, rubber, etc. The circular magnet fixed on the support member is provided between the upper side layer and the support member, and has a magnetic induction equal to or more than 100 mT. The circular magnet of each soft unit can be one or more, and the magnetic poles of two adjacent circular magnets are opposite to one another. Positioned at the center of the circular magnet, a coil has its center provided with an iron core and has an inductance of 30–80 mH. The sheet heater, which is fixed on the support member and has an impedance of 7–9$\Omega$ and a surface covered by an insulting layer, is provided between the lower side layer and the support member and is formed by a heating wire which is wrapped by a PVC insulting layer and twisted into a flat disc. The coil and the sheet heater are connected with the jack of main unit through the wire lead and the plug.

The panel unit according to the present invention can be used on the portions of the human body having relatively flat surface, e.g. foot sole and hand palm etc., and the soft unit is to be used on the portions of the human body which have a bend or curve surface, such as wrist, elbow, waist and knee etc. The panel unit and soft unit may be used in combination or separately depending upon the need. When the instrument is in use, the panel unit and/or soft unit has its plug(s) plugged into the jack of the main unit, and then power is switched on the main unit. The key-display system is then operated to select the pulse frequency and the heating temperature, the main unit outputs pulse current and heating current to the unit and the soft unit through the wire lead. Next, a pulse magnetic field is generated by the coil actuated by the pulse current and the heater panel is heated up by the heating current, releasing heat which causes the far infrared ceramic powder adhesive layer to emit far-infrared rays. As a result, a multiplex energy field is formed by the combination of a permanent magnetic field formed by the circular magnet having a magnetic induction intensity of 50~120 mT, far-infrared rays which have a wavelength of 8 μm~15μm, a pulse magnetic field which has a pulse magnetic induction intensity of ≧8 mT and the heat energy. Since the preferred embodiment according to the present invention has been chosen scientifically, it has the optimal matching parameter and adapts the far infrared rays, the permanent magnetic field, the pulse magnetic field and the thermal effect generated as above mentioned to the body so as to achieve the perfect effect of jingluo conduction and health care.

Since the present invention has a plurality of panel units and soft unit, several portions of the human body can be positioned into a multiplex energy field simultaneously making the jingluo conduction better, which can not be achieved by one unitary instrument with one complex energy field.

In summary, the present invention is a detachable combination health-care and treatment instrument having an optimal combination of the energy fields and an appropriate configuration suitable for the shapes of different portions of human body, being able to be applied simultaneously onto plural parts of the human body and possessing an energy field multiplexed by a permanent magnetic field, a pulse magnetic field, a thermal effect and far infrared rays.

BRIEF DESCRIPTION OF THE DRAWINGS

FIG. 4 is a partial sectional view of a soft unit of the present invention.

FIG. 5 is a schematic view for illustrating a circuit structure of the present invention.

DETAILED DESCRIPTION OF THE INVENTION

Figure 1:
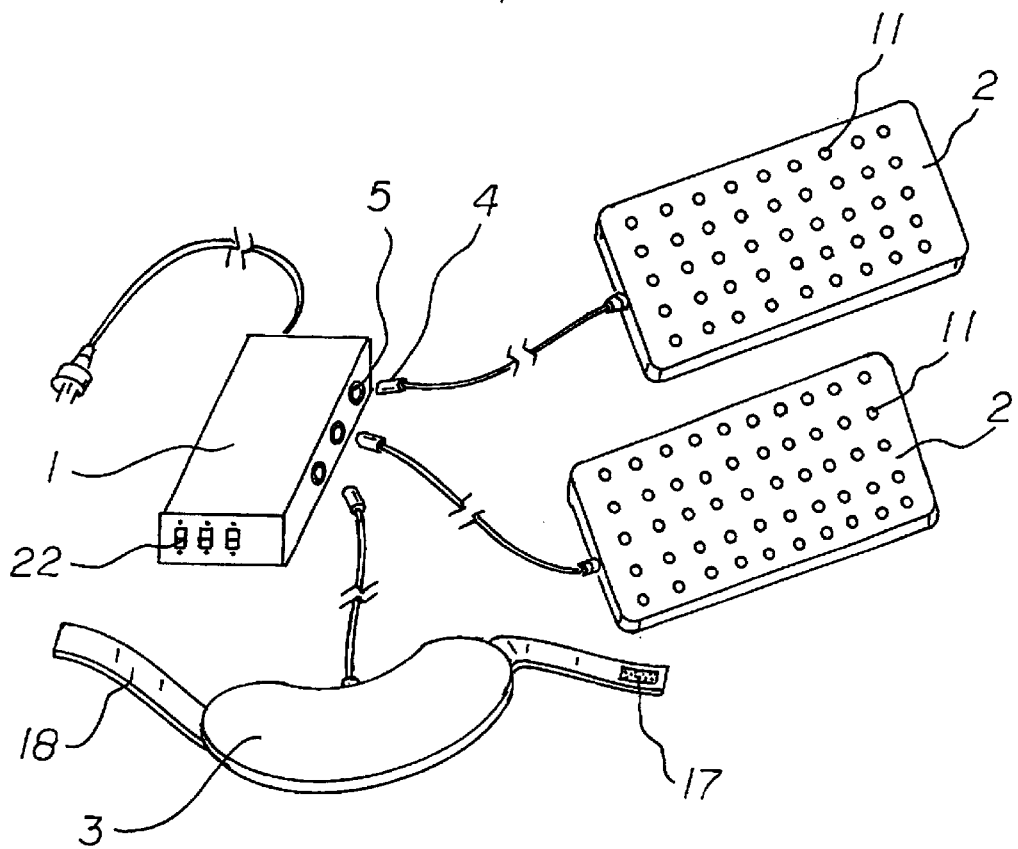
FIG. 1 is a schematic view showing the whole of the present invention.
Figure 2:
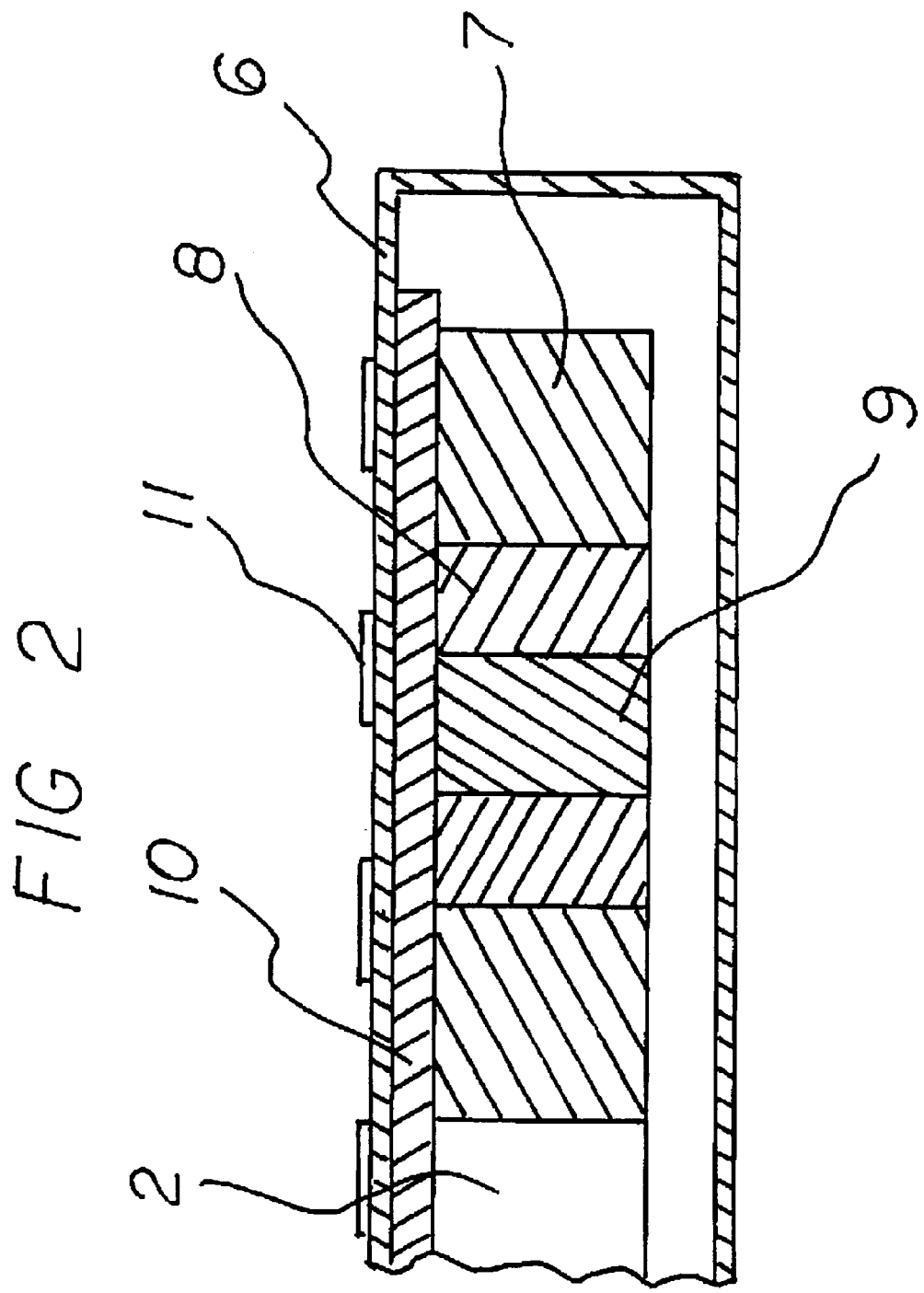
FIG. 2 is a partial sectional view of a panel unit of the present invention.
Figure 3:
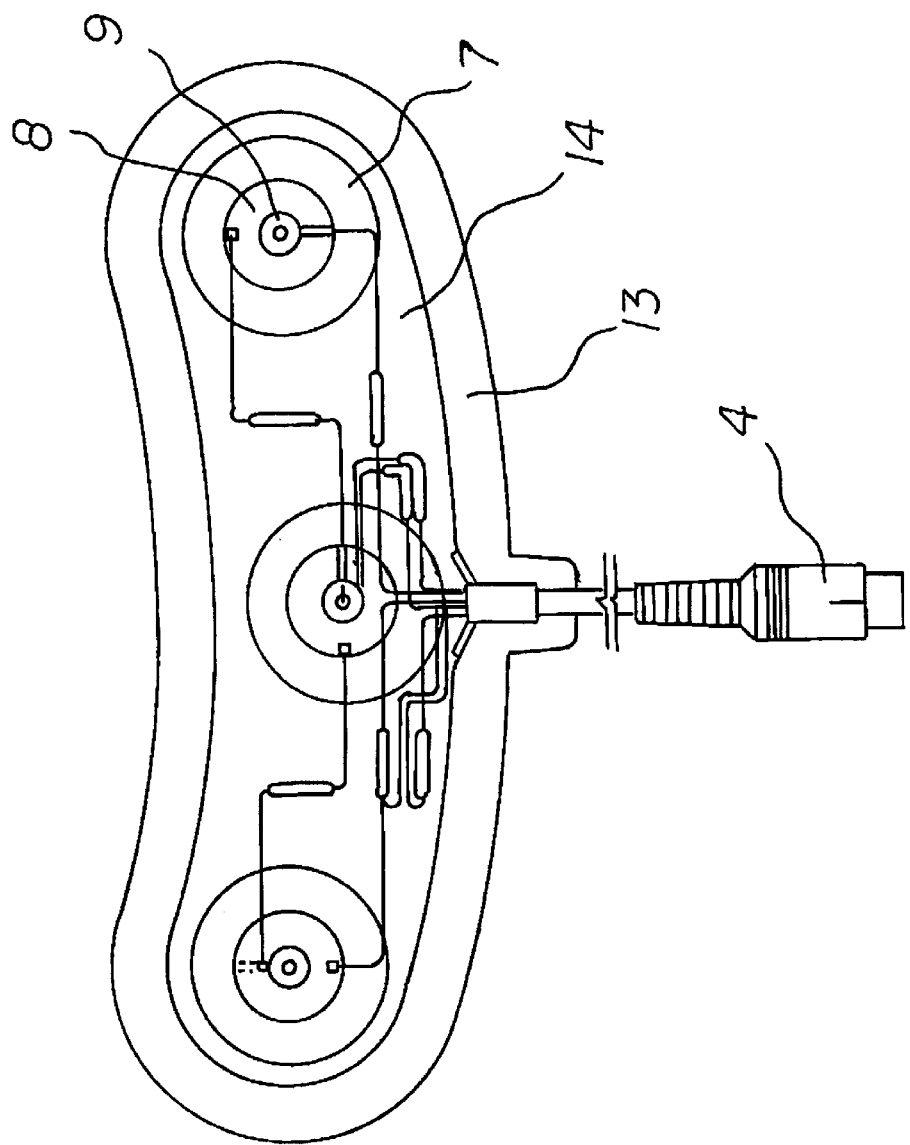
FIG. 3 is a schematic view of a support member and a circular magnet of the soft unit of the present invention.

The present invention is described in conjunction with FIGS. 1–5, in which 1 stands for the main unit, 2 for the panel unit, 3 for the soft unit, 4 for the plug, 5 for the jack, 6 for the shell, 7 for the circular magnet, 8 for the coil, 9 for the iron core, 10 for the heater panel, 11 for the far-infrared ceramic powder adhesive layer, 12 for the upper side layer, 13 for the lower side layer, 14 for the support member, 15 for the sheet heater, 16 for the heating wire having PVC, 17 for the nylon agraffe, 18 for a piece of band, 19 for the switch and power system, 20 for the temperature control system, 21 for the pulse magnetic control system and 22 for the key-display control system.

The shell 6 of the main unit 1 is rectangular in shape, which size is 200×180×88 mm and the parameters thereof are:

Input power voltage: AC220V±10%;
Input power frequency: 50 HZ±2%;
Input power rating: 160 W+10%;
Output form of magnetic pulse: square;
magnetic pulse frequency: high frequency: 50 HZ±15 HZ; low frequency: 1 HZ±0.3 HZ;

According to the preferred embodiment, two panel units 2 and one soft unit 3 are chosen to match main unit 1. The panel unit 2 and soft unit 3 are connected to the main unit 1 via plugs 4, leads, and jacks 5. The main unit also includes a shell, a switch and power system, a temperature control system, a pulse magnetic control system, and key-display control system, in which, the switch and power system can be adapted to alternating current (AC) and direct current (DC). When the switch and power system include a plug and a power adapter, the instrument can be used in a household and a vehicle.

The size of the panel unit 2 is preferably 280×150×25 mm. The far infrared ceramic powder adhesive layer 11 is coated on the upper side of the upper layer of the shell 6 of the panel unit 2, the wavelength of the far infrared ceramic powder is 8μm~15μm. Three circular magnets 7 are provided in each of the panel units 2 and the magnetic poles of adjacent two circular magnets are arranged opposite to each other, the specification of each circular magnet is: the magnetic induction intensity is 100 mT, the outer diameter is 55 mm, the inner diameter is 25 mm, the thickness is 11 mm. However, the magnetic induction intensity can be between 100–130 mT. Additionally, other numbers of magnets can be employed. A coil 8 is provided in the center of the circular magnet, an iron core 9 is provided in the center of the coil 8, the inductance of the coil is 40 mH. However, the coils and cores can have an inductance of between 30–80 mH. A heating wire, which is 1Ωm and 4 m in length, is arranged by twisting it into a flat disc on one side of the insulating panel, forming a heater panel 10. The heating panel can have an impedance of between 3–5Ω.

The shape of the soft unit 3 is of a long bean, and its size is 200×90×20 mm. The lower side layer 13 is made of a piece of cotton which is coated with a far infrared ceramic powder adhesive layer 11, the wavelength of the far infrared ceramic powder is 8μm~15μm. In the soft unit 3, a support member 14 is provided between the upper side layer 12 and the lower side layer 13. Three circular magnets 7 are provided in each soft unit 3 and the magnetic poles of adjacent two circular magnets are arranged opposite to each other. Again, the circular magnets can have coils and iron cores with an inductance of between 30–80 mH. Other numbers of magnets can also be used. The specification of the circular magnet is: the magnetic induction intensity is 110 mT, the outer diameter is 45 mm and the inner diameter is 25 mm. The induction intensity can be anything greater than or equal to 100 mT. The sheet heater 15, having an impedance of 8Ω, is formed by twisting a heating wire 16 wrapped by PVC insulting layer, the shape and the size of the sheet heater is like that of the support member. The sheet heater can have an impedance of between 7–9Ω. The lower side layer of the soft unit can also be formed from a fibre fabric containing containing a far infrared ceramic power. Leather can also be used. Other fabrics such as wood, hemp, chemical fiber coated with a far infrared ceramic power adhesive can also be used. Additionally, the support member can be formed from a tough material such as plastic or rubber.

A band 18 with nylon agraffe 17 is fixed on both ends of the soft unit.

The operation of the instrument according to the present invention is as follows: put two panel units 2 to the soles of the feet respectively, place the soft unit 3 onto the neck by the band 18 with nylon agraffe 17, then switch the power on and select a low frequency pulse and a low heating temperature. When the multiplex energy field comprising far infrared rays, a permanent magnetic field, a pulse magnetic field and the thermal effect is applied to the soles of feet and the neck simultaneously the fatigue and ache in the neck is relieved shortly and the effect of treatment is apparent and quick.

According to different symptoms, the panel units can be put on the palms, in addition, the soft unit can also be put on the waist, the elbow and the knee etc. All can get the good effect.

Thus, the panel unit according to the present invention can be used on the portions of the human body having relatively flat surface, e.g. foot sole and hand palm etc., and the soft unit is to be used on the portions of the human body which have a bend or curve surface, such as wrist, elbow, waist and knee etc. The panel unit and soft unit may be used in combination or separately depending upon the need. When the instrument is in use, the panel unit and/or soft unit has its plug(s) plugged into the jack of the main unit, and then power is switched on the main unit. The key-display system is then operated to select the pulse frequency and the heating temperature, the main unit outputs pulse current and heating current to the panel unit and the soft unit through the wire lead. Next, a pulse magnetic field is generated by the coil actuated by the pulse current and the heater panel is heated up by the heating current, releasing heat which causes the far infrared ceramic powder adhesive layer to emit far-infrared rays. As a result, a multiplex energy field is formed by combination of a permanent magnetic field formed by the circular magnet having a magnetic induction intensity of 50~120 mT, far-infrared rays which have a wavelength of 8$\mu$m~15$\mu$m, a pulse magnetic field which has a pulse magnetic induction intensity of $\geq$8 mT and the heat energy. Since the preferred embodiment according to the present invention has been chosen scientifically, it has the optimal matching parameter and adapts the far infrared rays, the permanent magnetic field, the pulse magnetic field and the thermal effect generated as above mentioned to the body so as to achieve the perfect effect of jingluo conduction and health care.

Since the present invention has a plurality of panel units and soft unit, several portions of the human body can be positioned into a multiplex energy field simultaneously making the jingluo conduction better, which can not be achieved by one unitary instrument with one complex energy field.

Furthermore, the frequency of the pulse magnetic field and the heating temperature can be chosen by a key-display system. Also, the magnetic field or heat can be chosen by a key-display system. The multiplex energy field can be formed by permanent field and pulse magnetic field or by permanent field, heat and far-infrared rays, so different combinations can be chosen when it is used.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A detachable combination health-care and treatment instrument having a main unit, panel units and soft units, and said main unit being connected with the panel unit and the soft unit by a lead, a plug and a jack respectively, wherein said main unit includes a shell, a switch and power system, a temperature control system, a pulse magnetic control system, and a key-display control system;

said panel unit includes a shell having a far-infrared ceramic powder adhesive layer coated on the upper side of the upper layer thereof, circular magnets each having magnetic induction intensity of 100–130 mT, coils and cores having an inductance of 30–80 mH, and a heater panel having an impedance of 3–5$\Omega$, and said soft unit includes an upper side layer, a lower side layer with a far-infrared ceramic powder adhesive layer on the outside, a support member, circular magnets each having magnetic induction intensity of $\geq$100 mT, coils and iron cores having an inductance of 30–80 mH, and a sheet heater having an impedance of 7–9 $\Omega$.

2. The detachable combination health-care and treatment instrument according to claim 1, wherein said instrument further includes a switch and power system to adapt the instrument to an alternating current power supply.

3. The detachable combination health-care and treatment instrument according to claim 1, wherein said instrument further includes a switch and power system to adapt the instrument to a direct current power supply.

4. The detachable combination health-care and treatment instrument according to claim 2, wherein said switch and power system includes a plug to a power supply and a power adapter.

5. The detachable combination health-care and treatment instrument according to claim 3, wherein said switch and power system includes a plug to a power supply and a power adapter.

6. The detachable combination health-care and treatment instrument according to claim 1, wherein the number of the circular magnets of each panel unit or soft unit can be one or more, and the magnetic pole directions of two adjacent circular magnets are opposite.

7. The detachable combination health-care and treatment instrument according to claim 1, wherein the lower side layer of the soft unit is a fibre fabric containing far infrared ceramic powder.

8. The detachable combination health-care and treatment instrument according to claim 1, wherein the lower side layer of the soft unit is a leather or a fabric, such as wood, hemp, chemical fiber etc., coated with a far infrared ceramic powder adhesive layer.

9. The detachable combination health-care and treatment instrument according to claim 1, wherein the support member of said soft unit is made of tough material such as plastic or rubber.

10. The detachable combination health-care and treatment instrument according to claim 1, wherein said heater panel of the panel unit is formed by twisting a heating wire to a disc flat on one side of the insulating panel.

11. The detachable combination health-care and treatment instrument according to claim 1, wherein said sheet heater of said soft unit is formed by twisting a heating wire which is wrapped by PVC insulting layer into a disc flat.

* * * * *